United States Patent [19]
Chu

[11] Patent Number: 5,540,498
[45] Date of Patent: Jul. 30, 1996

[54] CAM-OPERATED GRADIENT FORMER

[75] Inventor: Daniel Y. Chu, San Francisco, Calif.

[73] Assignee: Bio-Rad Laboratories, Inc., Hercules, Calif.

[21] Appl. No.: 282,241

[22] Filed: Jul. 29, 1994

[51] Int. Cl.⁶ ............................. B01F 15/02; G05D 11/02
[52] U.S. Cl. ................................. 366/160.4; 366/181.8; 74/569; 222/137; 222/309
[58] Field of Search ............... 366/160.1–160.5, 366/162.1, 162.3, 173.1, 176.1, 176.3, 181.6, 181.8, 182.2, 189, 255–258, 267, 268; 222/134, 137, 145.1, 309; 604/903; 74/89, 107, 569, 833; 417/429, 539

[56] References Cited

U.S. PATENT DOCUMENTS

| | | |
|---|---|---|
| 1,007,275 | 10/1911 | Desmond . |
| 2,737,978 | 3/1956 | Eberz . |
| 3,134,508 | 5/1964 | Bayer et al. . |
| 3,159,312 | 12/1964 | Van Sciver II ................... 222/137 |
| 3,799,406 | 3/1974 | St. John et al. ................... 222/309 |
| 4,233,156 | 11/1980 | Tsukada et al. . |
| 4,234,107 | 11/1980 | Geralein . |
| 4,352,636 | 10/1982 | Patterson et al. . |
| 4,503,721 | 3/1985 | Hietanen et al. . |
| 4,594,064 | 6/1986 | Anderson . |
| 4,595,495 | 6/1986 | Yotam et al. . |
| 4,734,187 | 3/1988 | Visentin et al. . |
| 4,828,148 | 5/1989 | Haluda et al. . |
| 4,874,368 | 10/1989 | Miller et al. ................... 222/137 X |
| 4,968,535 | 11/1990 | Terai et al. . |
| 4,986,443 | 1/1991 | Saur et al. ................... 222/137 X |
| 5,088,625 | 2/1992 | Farber et al. . |

FOREIGN PATENT DOCUMENTS

| | | |
|---|---|---|
| 0555119A1 | 1/1993 | European Pat. Off. . |
| 2172937 | 10/1986 | United Kingdom ................... 417/429 |

*Primary Examiner*—Charles E. Cooley
*Attorney, Agent, or Firm*—Townsend and Townsend and Crew

[57] ABSTRACT

Gradient gels for electrophoresis are produced by an apparatus in which a pair of syringes are mounted on a support rack together with cams arranged for synchronous rotation. Cam followers engaged by the cams are linked to the syringe barrels, with each cam defining a distinct spiral path translated by one of the cam followers into a preselected rate or rate profile of volumetric discharge from one of the syringes as the cam rotates. With the rate or rate profile established by one cam being distinct from the rate or rate profile established by the other, a gradient or other variation in composition is obtained when the syringe discharges are combined into a common stream and directed to the gel enclosure for solidification into a gel. The gradient or variation in composition is determined by the cam profiles alone, and is independent of the rate at which the cams are rotated, and of whether or not the rotation is performed in a steady manner. The apparatus can be readily designed for manual operation with highly accurate and reproducible results.

14 Claims, 7 Drawing Sheets

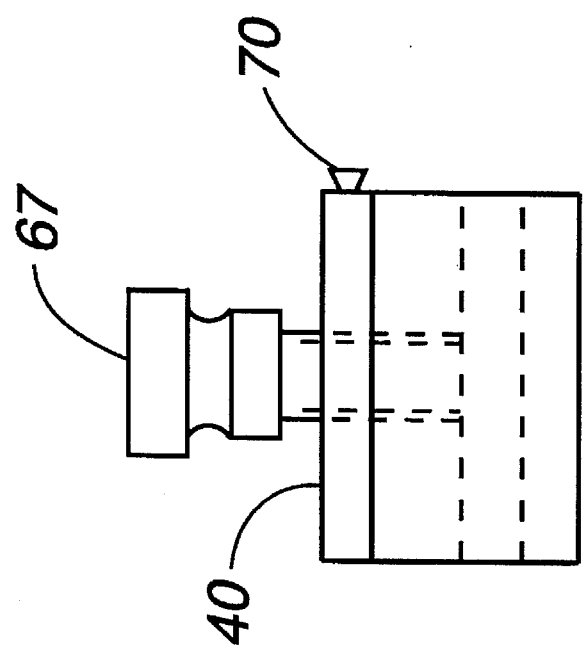
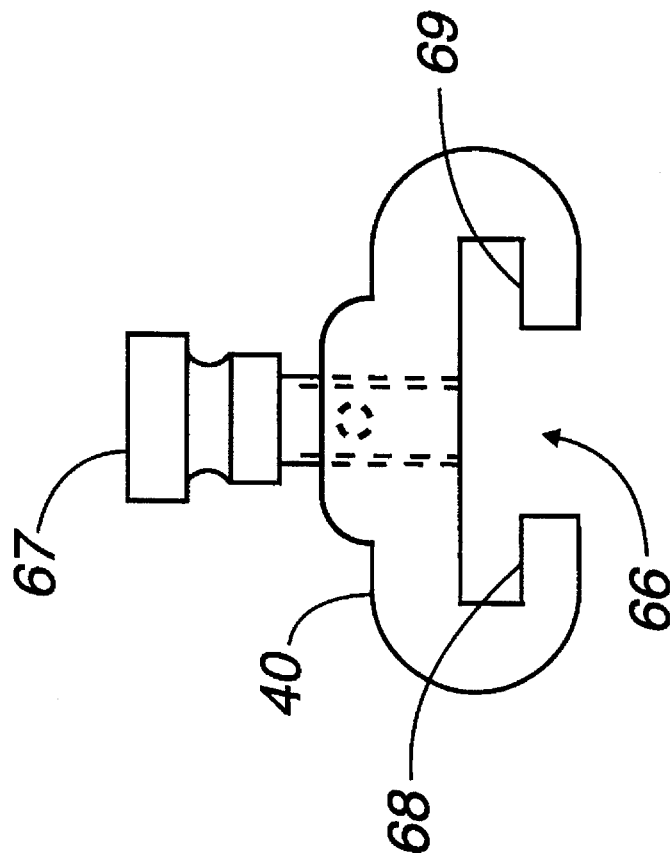
Fig. 5b
Fig. 5a

CAM-OPERATED GRADIENT FORMER

This invention relates to apparatus used in conjunction with electrophoresis, and in particular to apparatus for forming gradient gels used in certain electrophoretic processes.

BACKGROUND OF THE INVENTION

Electrophoresis is one of the most widely used techniques in biotechnology laboratories for analyzing mixtures of macromolecules, whether they be proteins, nucleic acids, carbohydrates or other species. Many electrophoretic procedures use a gel as a separation medium, and in many cases, greater sensitivity, range and versatility can be achieved by the use of a gradient gel, in which a characteristic of the gel is varied with the distance along one or more axes of the gel. Porosity gradients, for example, are useful in separating mixtures of a large number of components whose molecular weights vary over a wide range, since high molecular weight species require a relatively high gel porosity for separation from each other while low molecular weight species require a relatively low porosity. In gels containing a denaturant, a gradient is often formed in the concentration of the denaturant, particularly when the gel is used for separations of nucleic acids for DNA sequencing.

Gradients are useful in capillary or tube-shaped gels as well as slab gels. In slab gels, the gradients may be either parallel or perpendicular to the direction of migration, with useful results obtained in both cases. For example, denaturant gradients which are perpendicular to the direction of electrophoretic migration are useful in certain separations of nucleic acids to distinguish mutant genes from wild-type genes. Denaturant gradients which are parallel to the direction of separation are often used as the second stage of a two-dimensional separation, following a first stage where separation is performed in a constant gel. Linear gradients are most often used although nonlinear gradients are preferred in some cases. Stepwise variations are also useful.

The gradient may be formed by distributing the gel monomers and other components used in forming the gel between two source mixtures differing in concentration, then drawing from the two source mixtures at proportions which vary with time. For porosity gradients, the two source mixtures will vary in the concentration of the gel monomer, the crosslinking agent if one is used, or both. For denaturant gradients, the source mixtures will vary in the concentration of the denaturant. The method is simple in principle, but difficult to apply in a manner which results in a high degree of precision and reproducibility. In particular, for the laboratory technician who produces gradient gels for immediate use in the laboratory itself, there is a need for a simple device which can be used in the laboratory and which has a minimum of moving parts, yet is reliably precise and reproducible from one gel to the next.

These and other problems associated with prior art gradient formers are addressed by the present invention.

SUMMARY OF THE INVENTION

An apparatus has now been devised which uses cams to govern the travel of two syringe plungers in a unique arrangement which discharges liquids from the syringes at a volumetric ratio that varies in a manner established by the shapes of the cams. The liquids discharged from the syringes are combined into a common stream for feeding directly into the tube, capillary or slab space which serves as the gel enclosure, thereby producing a gradient gel in the enclosure.

The cams and the syringe barrels are mounted to a support rack, and movable linkages join the cams to the plungers. The cams define spiral paths which translate to linear movement of the plungers as the cams rotate. The spiral paths differ for each plunger so that the plungers are depressed at different rates. For syringe barrels of equal size, this results in different volumetric flow rates emerging from the syringes and a changing volumetric ratio. The profile of the volumetric ratio change, i.e., its variation as a function of the total amount of liquid discharged, is determined by the shapes of the cams, and any such profile can be achieved by appropriately shaped cams. The profile may therefore be a linear gradient, a nonlinear smooth curve gradient such as a hyperbolic curve, exponential curve or S-shaped curve, a segmented profile with one or more step increases or decreases and either a varying ratio or a constant ratio between steps, or any combination of these. The term "spiral path" is used herein to indicate any configuration in which the distance of path from the axis of rotation of the cam monotonically decreases as the cam rotates. At each point in time as the cams rotate, therefore, the syringe plungers either move further into the barrels or remain stationary.

The volumetric ratio profile achieved by the rotation of the cams is independent of the rate of rotation and independent of whether the rotation is constant or variable. Accordingly, the cams can be rotated either by a controlled power source or by hand, with equally effective results. The cams can both be on a single wheel or on separate wheels ganged together to rotate as a unit or joined through a gear train of determined ratio. As a particularly convenient means of assuring synchronous rotation, the cams are preferably formed on opposite sides of a common disk or wheel, arranged on the apparatus to be rotated by hand. Each cam can be a shoulder on the disk face, a ridge protruding from the disk face, or a groove cut into the disk face.

Each spiral path will span at least a portion of the full 360° rotation of the cam on which the spiral is formed, and in many cases the full 360° rotation of the cam. The spiral may also exceed 360°, overlapping itself, so that the plunger will continue to move inward relative to the syringe barrel as the cam is rotated beyond a full cycle.

Additional features included in preferred embodiments of the invention include cam followers arranged to translate the rotational motion of the cams to linear motion of the syringe plungers, and cam follower guides to limit the travel of the cam followers to a linear direction relative to the support rack, and hence relative to the barrels mounted on the rack. Further features include a selection or range of mounting locations on the support rack for the syringe barrels, each mounting location permitting the cams to impart a different range of motion to the plungers. Thus, the same degree of rotation of the cams can be made to translate into differing linear distances of motion of the plungers. This is useful either as a further means of controlling or varying the gradient produced, or to adapt the apparatus to the preparation of gels of different sizes.

Further features, embodiments and advantages of the invention will be apparent from the description which follows.

BRIEF DESCRIPTION OF THE DRAWINGS

FIGS. 5a and 5b are a side view and end view, respectively, of one of the plunger end caps of the gradient former of FIG. 1.

Figure 1:
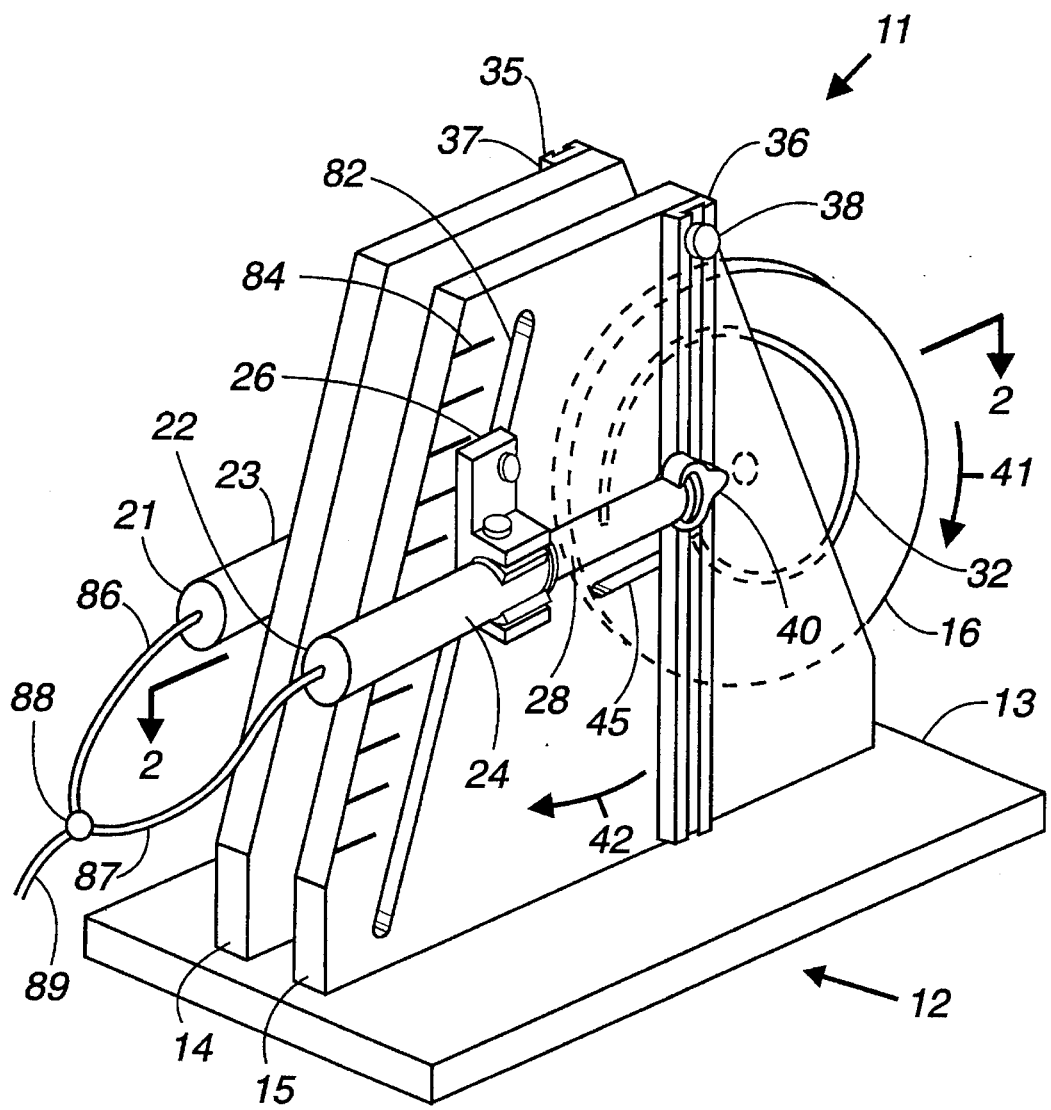
FIG. 1 is a perspective view of a gradient former in accordance with the present invention.

DETAILED DESCRIPTION OF THE
INVENTION AND PREFERRED
EMBODIMENTS

While the invention is generic in scope and can assume a wide range of implementations and embodiments, a better understanding of the invention, its components and their operation and coaction may be had by a detailed review of a single device constructed in accordance with the invention. This device is depicted in the drawings and discussed below.

Figure 2:
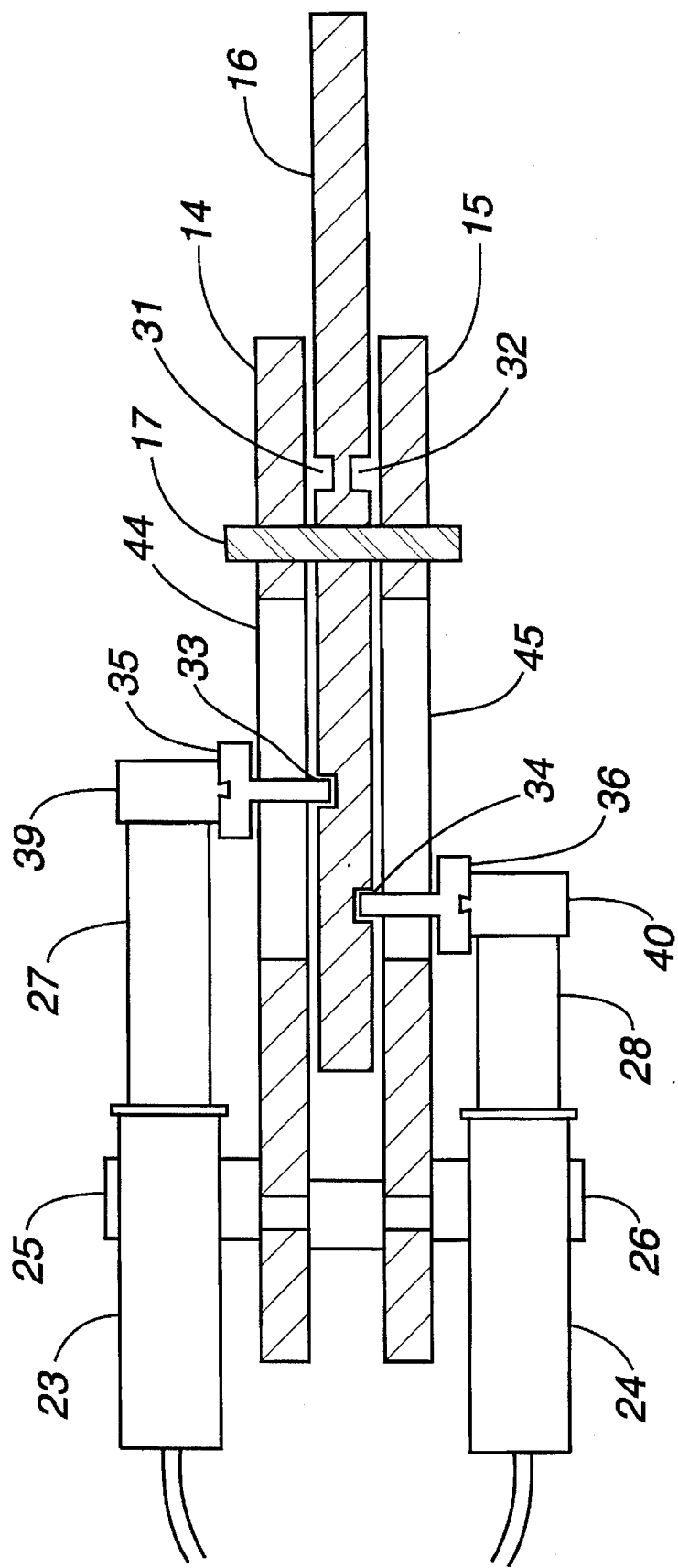
FIG. 2 is a cross section of the gradient former of FIG. 1 taken along line 2—2 of FIG. 1.

FIG. 1 shows the gradient former 11 in a perspective view. The apparatus consists of a support rack 12 consisting primarily of a horizontal base 13 and two plates 14,15 mounted vertically to the base and parallel to each other. A cam disk 16 is mounted to the two plates and positioned between them by an axle through its center, permitting free rotation of the disk. The relative positions of the plates 14, 15 and disk 16 are further seen in the cross section view of FIG. 2, which also shows the axle 17 of the disk.

Also mounted to the two plates 14, 15 are a pair of syringes 21, 22, one syringe mounted to the outer face of each of the two plates. The syringes are mounted by their barrels 23, 24, which are secured to the plates by barrel clamps 25, 26, only one of which 25 is visible in FIG. 1. The syringe plungers 27, 28 (plunger 28 being visible in FIG. 1) are movable within the barrels. The movement of the plungers is governed by the rotation of the cam disk 16.

The linkage which joins the cam disk 16 to each of the two syringe plungers includes:

two spiral grooves 31, 32, one on either face of the cam disk, pegs 33, 34 (visible in FIG. 2) loosely fitting inside the grooves to serve as cam followers, each peg mounted to the back side of one of two levers 35, 36, each lever pivotally mounted to the outer face of one of the two plates 14, 15 at pivot axes 37, 38, and plunger end clamps 39, 40 slidably mounted to the levers and clamping the outer ends of the plungers.

The cam disk 16 is mounted between the two plates 14, 15 of the support rack with the rim of the disk exposed to permit the user to turn the disk by hand. When the disk is turned in the direction indicated by the arrow 41 (FIG. 1), the spiral grooves 31, 32 on either side of the disk rotate in the same direction and cause the pegs 33, 34 to travel outward relative to the disk. The movement of the pegs causes the levers 35, 36 to pivot in the direction shown by the arrow 42. The pivoting of the levers causes the plunger end clamps 39, 40 and hence the plungers themselves 27, 28 to move in the direction shown by the arrow 43. The pegs 33, 34 extend through horizontal slots 44, 45 in the support rack plates 14, 15. The slots serve not only to permit the pegs to reach the grooves 31, 32, but also serve as guides for the travel of the pegs, limiting the travel to straight horizontal paths in a radial direction relative to the disk.

Figure 3B:
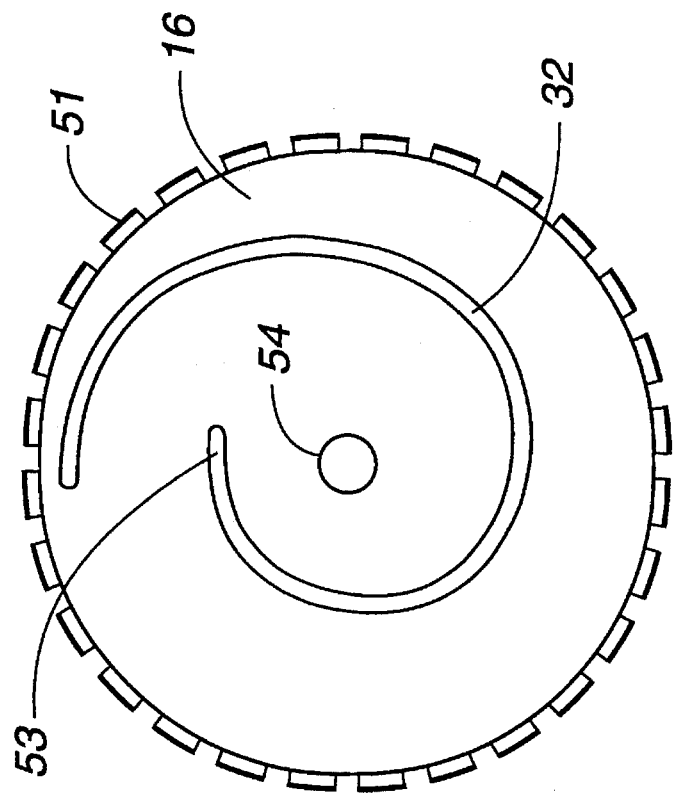
FIGS. 3a and 3b are plan views of the two faces of the cam disk of the gradient former of FIG. 1.
Figure 3A:
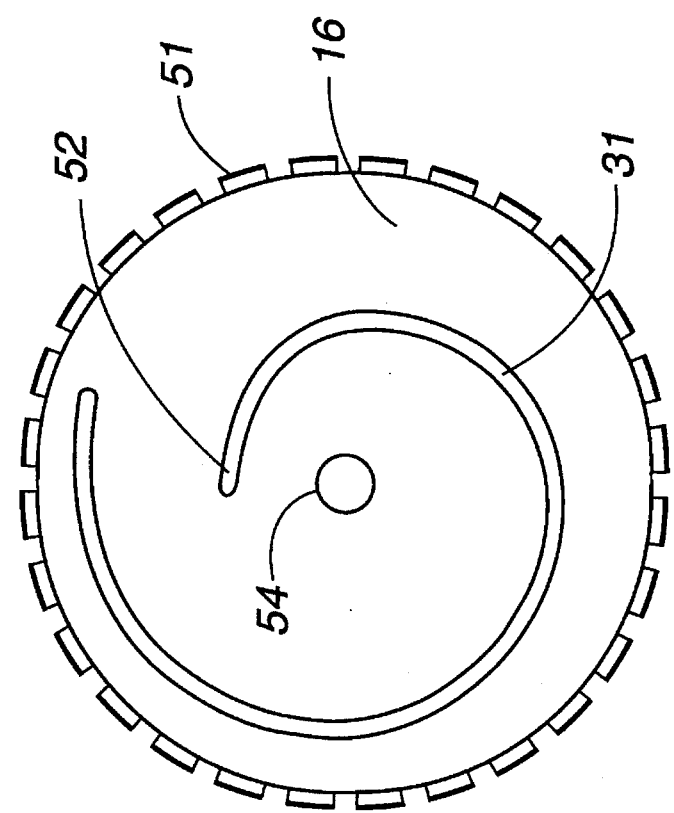

The shapes of the grooves on the disk can be seen in FIGS. 3a and 3b which show the two faces, respectively, of the disk. The rim 51 of the disk is knurled or otherwise contoured for an easy grip by the user's hand without a risk of slippage.

The cams themselves on this disk are grooves 31, 32. As mentioned above, however, alternative cams may be shoulders or ridges on the disk surfaces. The corresponding cam follower for a shoulder cam may be a peg or a roller mounted to the back of the lever, and the corresponding cam follower for a ridge cam would be a projection with a grooved end, likewise mounted to the back of the lever. Any of various other components and configurations which function in an analogous manner may be substituted to the same or an equivalent effect, as would be readily apparent to those skilled in the art.

Of the spiral grooves, the ends 52, 53 which are closest to the center 54 of the disk represent the starting points of the cam followers. As the disk rotates, each cam follower moves radially outward, causing the syringe plungers to advance into the barrels. The dissimilarity between the curvatures of the grooves results in different rates of advancement of the syringe plungers, and hence the particular profile of the volumetric ratio being discharged from the syringes. The grooves shown in this drawing are both smooth curves, i.e., the angular rate of change of the distance of the groove from the disk center is either constant or smoothly increasing or decreasing for each groove. As a result, the plungers advance at continuously and smoothly varying rates and thereby produce a smooth curve gradient in the resulting gel, whether that gradient be linear or nonlinear. Stepwise increases in the gel composition are achieved when one spiral curve has one or more sharp changes in curvature, i.e., a stepwise change in the angular rate of change of the distance of the groove from the center.

Figure 4C:
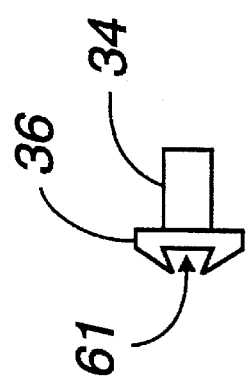
FIGS. 4a, 4b and 4c are a top view, side view and end view, respectively, of one of the lever component of the gradient former of FIG. 1.
Figure 4A:
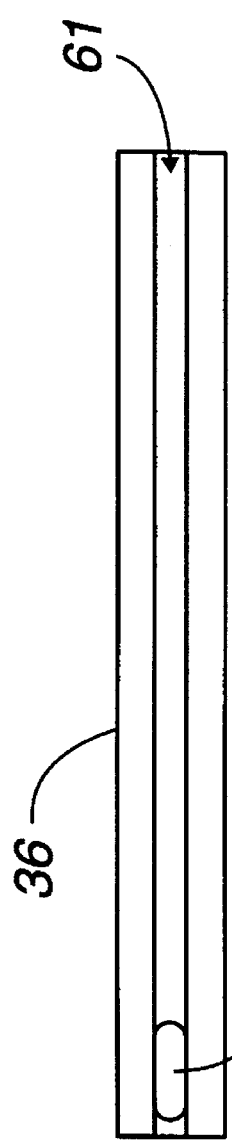
Figure 4B:
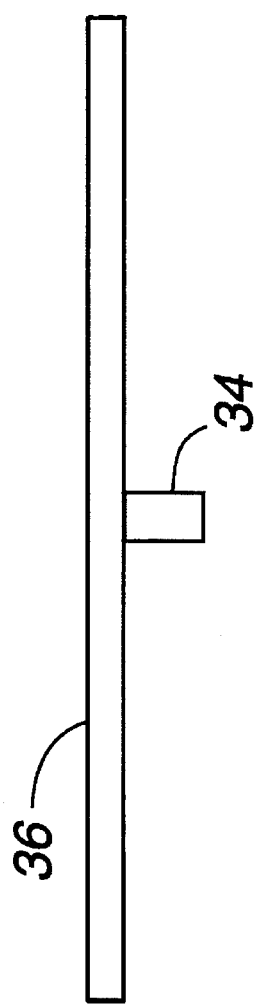

The lever 36, as shown in three views in FIGS. 4a, 4b and 4c, has a retaining groove 61 on its outer face to receive a flared projection from the plunger end cap (shown in a subsequent drawing and discussed below) and to allow the projection to slide along the lever. The retaining groove 61 has an opening which is narrower that the floor of the groove, thereby preventing the plunger end cap from becoming disengaged from the groove.

The peg 34 which serves as a cam follower is affixed to the face of the lever which is opposite that of the retaining groove. At its fulcrum, the lever contains a slot 62 to permit the passage of a bolt joining the lever to the support rack plate. The slot 62 is parallel to the longitudinal axis of the lever 36. Since the peg is immobile relative to the lever and is restricted to a straight line of travel relative to the support rack by the straight elongated guide 45 in the support rack plate (FIGS. 1 and 2), pivoting of the lever away from the vertical (in the direction of the arrow 45 in FIG. 1) results in sliding of the lever fulcrum 38 downward. The slot 62 accommodates this sliding motion while also permitting the pivotal rotation of the lever.

FIGS. 5a and 5b illustrate one of the plunger end caps 40 in detail. A retaining groove 66 in the end cap receives the end flange of a syringe plunger by sliding engagement. A clamping screw 67 forces the end flange against retaining shoulders 68, 69 inside the retaining groove 66 on either side, securing the end cap to the plunger. A knob 70 protruding from the rear surface of the end cap fits inside the retaining groove 61 in the outer face of the lever 36 (see FIGS. 4a and 4c) to slide along the groove. The knob is of an expanding diameter, such as for example the head of a countersink screw (the flared projection referred to above), to match the cross section of the retaining groove 61 in the lever and prevent disengagement.

Figure 6:
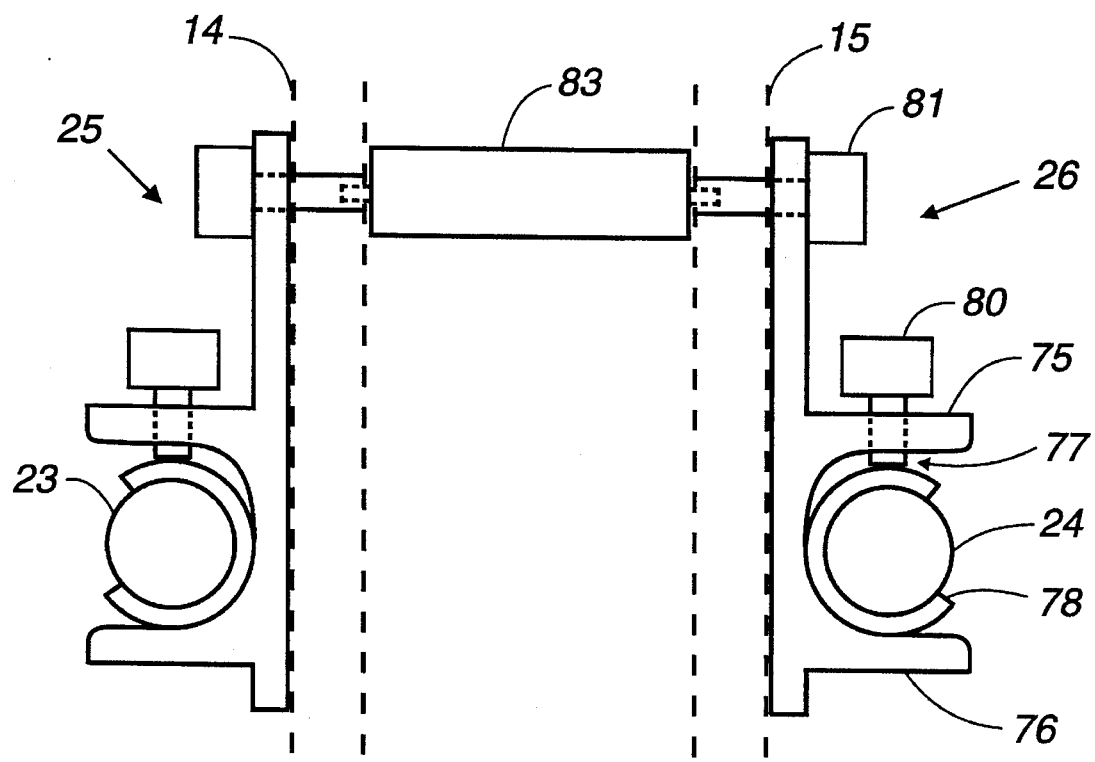
FIG. 6 is a side view of one of the barrel clamps of the gradient former of FIG. 1.

A side view of the two barrel clamps 25, 26 is provided by FIG. 6. Parallel shelf-like projections 75, 76 on each clamp form a recess 77. The syringe barrels 23, 24, each partially encased in a sleeve 78, is placed in the recess, and a tightening screw 80 secures the sleeve and syringe in place. The sleeve 78 serves to distribute the pressure of the tightening screw 80 over a larger area of the syringe barrel. The barrel clamp 26 is secured to the support rack plates 14, 15 by further clamping screws 81 which pass through openings in the plates and engage both ends of a threaded spacer 83 between the plates, the spacer holding the clamps in position while maintaining the distance between the plates.

As seen in FIG. 1, the opening through which the clamping screw extends to secure the barrel clamp to the plate is an elongated slot 82 which extends almost the full height of the plate. This slot, although straight, is at an acute angle relative to the horizontal guide slot 45 which sets the direction of travel of the cam follower. The barrel clamp 26 can thus be secured to the support rack at any location along this angled slot 82. Since the barrel clamp maintains the barrel 24 in a horizontal position, the plunger end cap 40 will then move along the lever 36 to the same height as the barrel clamp, thereby maintaining the syringe plunger and the barrel in horizontal alignment. The range of linear distance that the plunger end cap 40 will travel will vary with the position of the cap along the length of the plunger. The peg 34 which serves as the cam follower is fixed to the lever, however, and its range of motion as a result of the cam rotation remains constant regardless of the vertical location of the syringe barrel. Full travel of the peg 34 from one end of the guide slot 45 to the other will therefore translate into a variable distance of travel for the plunger depending on the height of the syringe. In this manner, the operator can select the total volume of liquid discharged from each syringe by a full cycle of the cam disk 16 by simply placing the syringe (i.e., securing the barrel clamp) at an appropriate height on the support rack. A graduated scale 84 assists the operator in correlating the total volume discharged from the syringes with the position of the barrel clamp.

Figure 7A:
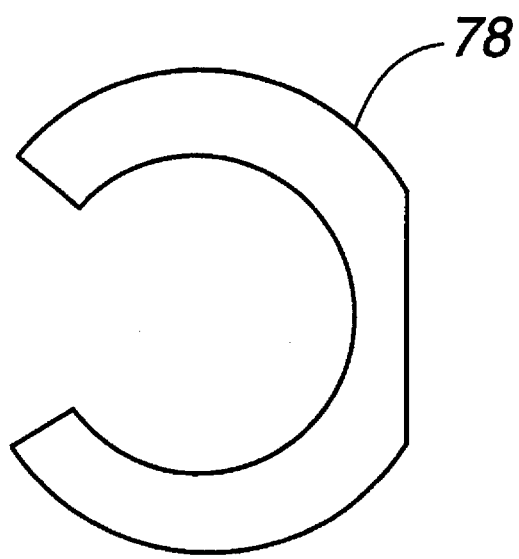
FIGS. 7a and 7b are end views of two interchangeable syringe barrel sleeves for use as part of the gradient former of FIG. 1.
Figure 7B:
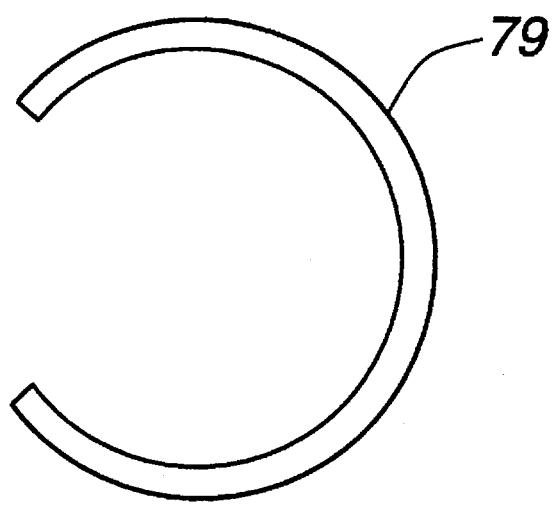

Another method of changing the total volume of liquid discharged when the cam disk is rotated a full cycle is by replacing one syringe with another of a different volumetric capacity. To do this without also substituting a different barrel clamp, one can replace the sleeve with a sleeve of a different thickness. FIGS. 7a and 7b, for example, illustrate end views of two sleeves 78, 79, respectively, with the same outer diameter but different thicknesses to accommodate syringe barrels of two different outer diameters.

Returning finally to FIG. 1, discharge tubing 86, 87 from each of the two syringes meets at a Y-fitting 88 where the two discharge streams are combined into a common stream 89 which is then fed directly to the gel enclosure.

An example of the curvatures of the two spiral paths shown in FIGS. 3a and 3b is set forth in the following table. The spiral paths set out in the table are for a cam disk having a radius of about 3.25 inches (8.26 cm) with cam distances from the center of the disk ranging from 1.250 inches (3.2 cm) to 2.7 inches (6.9 cm). The spirals are shaped to produce a constant gradient gel whose composition varies in a linear manner from 100% of the composition of one syringe (Syringe A) to 100% of the composition of the other (Syringe B) over a full 360° rotation of the cam disk. Cam A controls the movement of Syringe A while Cam B controls the movement of Syringe B.

| | Cam Profiles for Linear Gradient 0 to 100% | | |
|---|---|---|---|
| Arc | Proportion of Syringe B Solution in Combined Stream | Cam Distance From Center of Disk (inches) | |
| (degrees) | (percent) | Cam A | Cam B |
| 0 | 0 | 1.250 | 1.250 |
| 20 | 5.56 | 1.407 | 1.255 |
| 40 | 11.11 | 1.556 | 1.268 |
| 60 | 16.67 | 1.695 | 1.291 |
| 80 | 22.22 | 1.826 | 1.322 |
| 100 | 27.78 | 1.947 | 1.363 |
| 120 | 33.33 | 2.060 | 1.412 |
| 140 | 38.89 | 2.163 | 1.471 |
| 160 | 44.44 | 2.258 | 1.538 |
| 180 | 50.00 | 2.343 | 1.615 |
| 200 | 55.56 | 2.420 | 1.700 |
| 220 | 61.11 | 2.487 | 1.795 |
| 240 | 66.67 | 2.546 | 1.898 |
| 260 | 72.22 | 2.595 | 2.011 |
| 280 | 77.78 | 2.636 | 2.132 |
| 300 | 83.33 | 2.667 | 2.263 |
| 320 | 88.89 | 2.690 | 2.402 |
| 340 | 94.44 | 2.703 | 2.551 |
| 360 | 100.00 | 2.707 | 2.709 |

In general, it will be readily apparent to those skilled in the art that still further variations may be made in the shapes and configurations, operating methods and other parameters of the system described herein without departing from the spirit and scope of the invention. Accordingly, the foregoing is offered primarily for purposes of illustration.

What is claimed is:

1. Apparatus for combining two fluids into a common stream at a volumetric ratio which varies in a preselected manner as the volume of said fluids thus combined increases, said apparatus comprising:

a support rack;

first and second syringes, each having a barrel and a plunger, and means for mounting said barrels to said support rack;

cam means rotatably mounted to said support rack, said cam means defining two dissimilar spiral paths arranged for synchronous rotation with said cam means;

first and second cam followers, each movably mounted to said support rack;

first and second plunger retainers joined to said first and second cam followers, respectively, each said plunger retainer adapted to engage one of said plungers and to impart movement to said plungers relative to said barrels at dissimilar rates in accordance with said dissimilar spiral paths; and tubing means extending from said barrels and combining fluid ejected from said barrels into a common stream.

2. Apparatus in accordance with claim 1 in which said first and second cam followers are each movably mounted to said support rack through intermediary members pivotally mounted to said support rack, and said first and second plunger retainers are joined to said first and second cam followers respectively through said intermediary members.

3. Apparatus in accordance with claim 2 in which said cam means are comprised of a single disk mounted between said first and second syringes, said spiral paths are defined by spiral grooves on opposite faces of said disk, and said cam followers are pins projecting from said intermediary members and received within said spiral grooves.

4. Apparatus in accordance with claim 2 in which said plunger retainers are mounted to said intermediary members in slidable manner to permit mobility of said plunger retainers relative to said intermediary members.

5. Apparatus in accordance with claim 2 further comprising guides in said support rack governing the travel of said first and second cam followers.

6. Apparatus in accordance with claim 5 in which said cam means are comprised of a single circular disk and said guides limit the travel of said first and second cam followers to straight lines that are radial relative to said circular disk.

7. Apparatus in accordance with claim 6 in which said straight lines are parallel to said barrels of said syringes when said barrels are mounted to said support rack.

8. Apparatus in accordance with claim 2 in which said cam followers are immovably affixed to said intermediate members and each intermediate member is both slidably and pivotally mounted to said support rack.

9. Apparatus in accordance with claim 1 in which said cam means are comprised of a single disk mounted between said first and second syringes, and each spiral path is defined by a ridge or a groove on a separate face of said disk.

10. Apparatus in accordance with claim 9 in which said disk is arranged on said support rack for manual access, thereby permitting hand rotation of said disk.

11. Apparatus in accordance with claim 9 in which said spiral paths are defined by spiral grooves on opposite faces of said disk.

12. Apparatus in accordance with claim 1 in which each plunger has an outer end terminating in a flange, and said plunger retainers are caps shaped to capture said flanges.

13. Apparatus in accordance with claim 1 in which said first and second plunger retainers are joined to said first and second cam followers respectively through levers having pivot axes at which said levers are pivotally mounted to said support rack, and said barrels are mountable to said support rack at any of multiple locations on said support rack, each at varying distances from said pivot axes, thereby providing said plungers with a varying range of motion relative to said barrels.

14. Apparatus in accordance with claim 1 in which said means for mounting said barrels to said support rack includes a plurality of interchangeable sleeves differing in thickness to receive syringe barrels differing in diameter.

\* \* \* \* \*